(12) United States Patent
Zheng et al.

(10) Patent No.: US 11,413,471 B2
(45) Date of Patent: Aug. 16, 2022

(54) CENTRAL NERVE MAGNETIC STIMULATION DEVICE AND HEALTHCARE OR MEDICAL INSTRUMENT HAVING SAME

(71) Applicants: BEIJING ALDANS BIOTECH CO., LTD, Beijing (CN); Yunfeng Zheng, Beijing (CN)

(72) Inventors: Yunfeng Zheng, Beijing (CN); Kui Geng, Beijing (CN)

(73) Assignee: Yunfeng Zheng, Beijing (CN)

( * ) Notice: Subject to any disclaimer, the term of this patent is extended or adjusted under 35 U.S.C. 154(b) by 29 days.

(21) Appl. No.: 17/041,618

(22) PCT Filed: Mar. 26, 2019

(86) PCT No.: PCT/CN2019/079655
§ 371 (c)(1),
(2) Date: Sep. 25, 2020

(87) PCT Pub. No.: WO2019/184904
PCT Pub. Date: Oct. 3, 2019

(65) Prior Publication Data
US 2021/0023380 A1   Jan. 28, 2021

(30) Foreign Application Priority Data
Mar. 26, 2018 (CN) .......................... 201810253246.8

(51) Int. Cl.
*A61N 2/00* (2006.01)
*A61N 2/02* (2006.01)

(52) U.S. Cl.
CPC ............... *A61N 2/006* (2013.01); *A61N 2/02* (2013.01)

(58) Field of Classification Search
CPC ........ A61N 2/002; A61N 2/004; A61N 2/008; A61N 2/006; A61N 2/02
See application file for complete search history.

(56) References Cited

U.S. PATENT DOCUMENTS

| | | | | |
|---|---|---|---|---|
| 2011/0125203 A1* | 5/2011 | Simon | ....................... | A61N 1/40 607/2 |
| 2016/0144175 A1* | 5/2016 | Simon | .................... | G16H 20/40 607/46 |

FOREIGN PATENT DOCUMENTS

| | | |
|---|---|---|
| CN | 1879906 A | 12/2006 |
| CN | 102309817 A | 1/2012 |
| CN | 107551403 A | 1/2018 |

OTHER PUBLICATIONS

State Intellectual Property Office of the P. R. China, International Search Report, dated Jun. 7, 2019.
(Continued)

*Primary Examiner* — Christine H Matthews
(74) *Attorney, Agent, or Firm* — Bay State IP, LLC (57) ABSTRACT

A central nervous magnetic stimulation device and a healthcare or medical instrument, wherein the device comprises a power source, a control circuit and a coil component, the control circuit comprising a main control chip and a main circuit, the power source supplying power to the control circuit, and the control circuit outputting a time-varying current to the coil component to generate a corresponding time-varying magnetic field. The area of the time-varying magnetic field matches with the size of a head, and the time-varying current is output at a frequency above 2000 Hz, and constitutes a string of rhythmic cluster-like bursts at an appropriate duty ratio or forms an envelope in a difference frequency way to output rhythm characteristics. The device can apply to the brain a magnetic stimulation with a weak intensity and high-frequency carrier wave, rhythmic cluster-like bursts and an approximately uniform magnetic field intensity distribution.

11 Claims, 4 Drawing Sheets

(56) References Cited

OTHER PUBLICATIONS

State Intellectual Property Office of the P. R. China, Written Opinion of the International Searching Authority, dated Jun. 14, 2019.

* cited by examiner

CENTRAL NERVE MAGNETIC STIMULATION DEVICE AND HEALTHCARE OR MEDICAL INSTRUMENT HAVING SAME

CROSS REFERENCE TO RELATED APPLICATION

This application is for entry into the U.S. National Phase under § 371 for International Application No. PCT/CN2019/079655 having an international filing date of Mar. 26, 2019, and from which priority is claimed under all applicable sections of Title 35 of the United States Code including, but not limited to, Sections 120, 363, and 365(c) and which in turn claims priority under 35 USC 119 to Chinese Patent Applications No. 201810253246.8 filed on Mar. 26, 2018.

TECHNICAL FIELD

The disclosure relates to the technical field of treatment equipment of central nervous system, in particular to a central nervous magnetic stimulation device, further to a healthcare or medical instrument having the central nervous magnetic stimulation device.

BACKGROUND ART

Central nervous system diseases or mental diseases are a large class of chronic brain diseases. At present, in addition to medication and psychological treatment, physical factor treatment is mainly achieved by electrical stimulation or magnetic stimulation.

Wherein, magnetic stimulation technology takes TMS (Transcranial Magnetic Stimulation) or rTMS (repetitive Transcranial Magnetic Stimulation) as a main development field. Compared with side effects of electrical stimulation, such as pain, convulsions, and memory loss, the magnetic stimulation has characteristics of being painless, non-invasive, and non-contacting, and efficacy of the magnetic stimulation in clinical treatment has been continuously discovered. As a result, application fields of the magnetic stimulation are expanding.

Because magnetic induction intensity decays exponentially with distance, it is difficult for existing instruments to effectively stimulate a deep brain, or apply a super-strong stimulation to the brain surface for an effective stimulation to the deep brain, which cannot achieve good biological effects. In addition, a high-intensity magnetic field is not suitable for home use considering focusing and safety issues. And there is a risk of epilepsy if the high-intensity magnetic field is used for the whole brain without a precise location.

Therefore, how to improve the existing central nervous magnetic stimulation device to achieve better biological effects, as well as a safer and more convenient use, is a technical problem to be solved by those skilled person in the art at present.

SUMMARY

The disclosure intends to provide a central nervous magnetic stimulation device. The central nervous magnetic stimulation device can apply to the brain a magnetic stimulation with a weak intensity, and rhythmic cluster-like bursts, which has an approximately uniform magnetic field intensity distribution and can reach the deep brain, to achieve better biological effects. The disclosure further intends to provide a medical instrument having the central nervous magnetic stimulation device.

To solve the above technical problem, the disclosure provides a central nervous magnetic stimulation device, comprising a power source, a control circuit and a coil component; wherein, the control circuit comprises a main control chip and a main circuit, the power source supplies power to the control circuit, and the control circuit outputs a time-varying current to the coil component to generate a corresponding time-varying magnetic field; wherein an action area of the time-varying magnetic field matches with a size of a human head; wherein the time-varying current is output at a frequency above 2000 Hz, and constitutes a string of a rhythmic cluster-like bursts at an appropriate duty ratio.

The disclosure further provides another central nervous magnetic stimulation device, comprising a power source, a control circuit and a coil component; wherein, the control circuit comprises a main control chip and a main circuit, the power source supplies power to the control circuit, and the control current to the coil component to generate a corresponding time-varying magnetic field; wherein an action area of the time-varying magnetic field matches with a size of a human head, and the time-varying current is output at a frequency above 2000 Hz, and forms an envelope in a difference frequency way to output rhythm characteristics.

With respect to said central nervous magnetic stimulation device, a rhythmic output of the time-varying current has an appropriate intermittent characteristic.

With respect to said central nervous magnetic stimulation device, the coil component comprises a plurality of coils, and outputs of the coils are independent to each other.

With respect to said central nervous magnetic stimulation device, the coils generate outputs synchronously, or the plurality of coils are divided into several groups, and coils in each group generate outputs synchronously or in the difference frequency way.

With respect to said central nervous magnetic stimulation device, when the plurality of coils are divided into several groups, different groups output rhythm characteristics synchronously at an appropriate duty ratio, or output rhythm characteristics by forming an envelope of superimposed magnetic fields in the difference frequency way.

With respect to said central nervous magnetic stimulation device, the coil component specifically comprises three coils corresponding to positions of temporal lobes on both sides of the brain and occipital lobe respectively, corresponding to positions of temporal lobes on both sides of the brain and parietal lobe respectively, or corresponding to positions of temporal lobes on both sides of the brain and frontal lobe respectively.

With respect to said central nervous magnetic stimulation device, the coil component specifically comprises two coils corresponding to left and right sides of the brain respectively, or corresponding to positions of occipital lobe and parietal lobe respectively.

With respect to said central nervous magnetic stimulation device, the coil component specifically comprises two coils located at the top of the head in parallel.

With respect to said central nervous magnetic stimulation device, the coil component comprises two coil groups, each of the coil groups comprises two coils corresponding to left and right sides of the brain respectively, corresponding to positions of occipital lobe and parietal lobe respectively, or located at the top of the head in parallel;

the two coil groups are partially overlapped or not overlapped, and the two coil groups generate outputs synchronously or in the difference frequency way.

With respect to said central nervous magnetic stimulation device, a diameter of the coil is larger than an outer diameter of the human brain, and a distance between the two coils is larger than a radius of the coil and less than 3 times of the radius of the coil.

With respect to said central nervous magnetic stimulation device, a waveform of the time-varying current is a trapezoidal wave, a sine wave, or a triangle wave, and the time-varying magnetic field is one waveform or a combination of two or more waveforms.

With respect to said central nervous magnetic stimulation device, a waveform of the time-varying magnetic field generated by the coil component has a rising edge and/or a falling edge.

With respect to said central nervous magnetic stimulation device, the waveform of the time-varying magnetic field has a rising edge and a falling edge, and there is a platform between the rising edge and the falling edge.

With respect to said central nervous magnetic stimulation device, a duration corresponding to the platform tends to zero.

With respect to said central nervous magnetic stimulation device, a rhythm of the string of the rhythmic cluster-like bursts is specifically a delta rhythm, a theta rhythm, an alpha rhythm, a beta rhythm, or a gamma rhythm of brain waves.

With respect to said central nervous magnetic stimulation device, a frequency of the time-varying current is in the range of 2000-20000 Hz.

With respect to said central nervous magnetic stimulation device, the frequency of the time-varying current is about 2500 Hz.

With respect to said central nervous magnetic stimulation device, the frequency of the time-varying current is about 20,000 Hz.

With respect to said central nervous magnetic stimulation device, a waveform of the time-varying current is unipolar or bipolar.

With respect to said central nervous magnetic stimulation device, the power source supplies the control circuit with a direct current voltage of 60V or less.

With respect to said central nervous magnetic stimulation device, the power source supplies the control circuit with a direct current voltage of 12 to 24V.

With respect to said central nervous magnetic stimulation device, a peak intensity of the time-varying magnetic field is greater than 0.5 Gs and less than 100 Gs within the action area, and a change rate of the peak intensity of the time-varying magnetic field over time dB/dt within the action area is less than 35 T/s.

With respect to said central nervous magnetic stimulation device, a maximum value of the peak intensity of the time-varying magnetic field within the action area matching the brain is greater than 0.5 Gs and less than 20 Gs.

The disclosure further provides a healthcare or medical instrument, comprising a central nervous magnetic stimulation device as described in any one of above embodiments.

The disclosure further provides a healthcare or medical instrument, comprising a central nervous magnetic stimulation device as described in any one of above embodiments. The healthcare or medical instrument used in combination with medicine is configured to improve brain function, prevent or treat brain diseases, enhance the effect of medicine or reduce side effects caused by medicine.

The central nervous magnetic stimulation device provided by the disclosure outputs a time-varying current to the coil component through the control circuit, so that the coil component can generate a time-varying magnetic field, wherein the area where the time-varying magnetic field is located is adapted to the size of the head, to form a magnetic field with uniform magnetic field intensity within the entire area of the head, so as to produce a better magnetic stimulation effect on the entire brain. At the same time, the time-varying current is output at a frequency above 2000 Hz, and constitutes a rhythmic string at an appropriate duty ratio, or forms an envelope in the difference frequency way to output rhythm characteristics. With such a design, a relatively smaller peak current and a weaker peak magnetic field intensity can be used to achieve a same or even better biological effects. The central nervous magnetic stimulation device can be used to manufacture healthcare or medical instruments to better improve brain health or treat brain diseases, and to reduce an operation noise of the product, so as to bring a better user experience.

Magnetic stimulation with appropriate parameters can improve brain function. Most of prior magnetic stimulation devices focus a magnetic field on a certain position of the brain, and adopts high-intensity magnetic field to induce the burst of action potentials of nerve cells, to achieve a purpose of diagnosis and treatment of brain diseases. However, the comprehensive analysis of the latest scientific research results prompts us that: a deep brain-reachable magnetic stimulation with a high frequency, rhythmic cluster-like bursts and weak intensity is expected to solve the neuroscience problems better. For example, many central nervous system dysfunctions or diseases, such as insomnia or Alzheimer's disease, may be related to hypofunction of inhibitory nerve cells or inhibitory neural circuits. Therefore, a selective improvement of a function of the inhibitory nervous system may help to improve brain function, and the deep brain-reachable magnetic stimulation with a weak-intensity, high-frequency and rhythmic, cluster-like bursts is expected to achieve the purpose of an selective improvement of functions of inhibitory nerve cells or inhibitory neural circuits, to be more effective, have fewer side effects, be easier for industrial implementation, and improve the user experience.

The healthcare or medical instrument provided by the disclosure, comprising the above central nervous magnetic stimulation device, has the same technical effect aforementioned, which will not be repeated here.

BRIEF DESCRIPTION OF THE DRAWINGS

Wherein, following components are shown in FIGS. 1-3: control circuit 101, power source 102, coil component 103, and coil 131.

DETAILED DESCRIPTION OF THE EMBODIMENTS

The disclosure intends to provide a central nervous magnetic stimulation device. The central nervous magnetic stimulation device can apply to the brain a weak-intensity and high-frequency magnetic stimulation with rhythmic cluster-like bursts, which has an approximately uniform magnetic field intensity distribution and can reach the deep brain, to achieve better biological effects and reduce noise to improve user experience.

Since a magnetic stimulation with appropriate parameters can improve brain function, the disclosure provides a central nervous magnetic stimulation device in order to obtain better biological effects.

In order for those skilled person in the art to better understand the solution of the disclosure, the disclosure will be further described in details below with reference to the accompanying drawings and specific embodiments.

Figure 1:
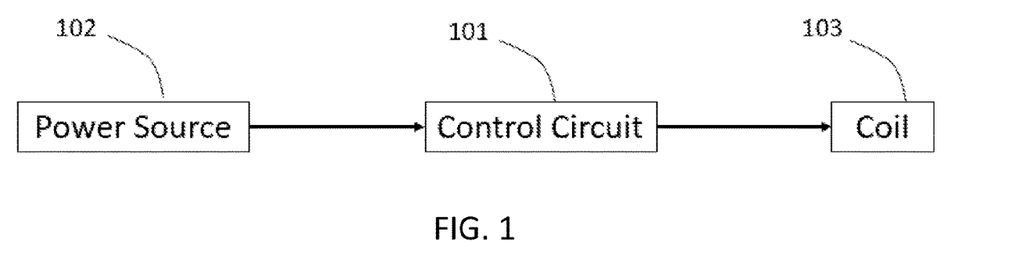
FIG. 1 illustrates a structural block diagram of a central nervous magnetic stimulation device provided by the disclosure, according to an embodiment.

Please refer to FIG. 1, which illustrates a structural block diagram of a central nervous magnetic stimulation device provided by the disclosure, according to an embodiment.

As shown in FIG. 1, the central nervous magnetic stimulation device comprises a power source 102, a control circuit 101 and a coil component 103; wherein, the control circuit 101 comprises a main control chip and a main circuit, the power source 102 is configured to supply power to the control circuit 101, and the control circuit 101 can output a time-varying current to the coil component 103 to generate a corresponding time-varying magnetic field in a target area.

In this embodiment, the target area, i.e. the action area of the time-varying magnetic field with an approximately uniform magnetic field intensity distribution induced by the coil component 103, matches with the size of the human head, and the control circuit 101 outputs to the coil component 103 a time-varying current with a frequency above 2000 Hz, which constitutes a string of rhythmic cluster-like bursts at a set duty ratio, or forms an envelope in a difference frequency way to output rhythm characteristics.

Wherein, the rhythmic cluster-like bursts refer to a rhythm of a current waveform formed by an alternating occurrence of continuous outputs during a period of time while continuous no-output during another period of time, wherein the continuous outputs during a period of time are defined as occupancy, while the continuous no-output during another period of time is defined as empty.

Specifically, the specific values of the occupancy and the empty, or the specific value of the duty ratio, can be determined after basic and clinical research, preset in the main control chip of the control circuit 101, assigned in a wireless communication way, or designed or selected by actual users according to usage requirements.

When to be specifically set, the rhythmic output of the time-varying current can also has an appropriate intermittent characteristic, such as 8-second pause per 2-second output.

When to be actually designed, the frequency of the time-varying current can be selected in the range of 2000-20000 Hz, and the frequency of the time-varying current can be specifically selected from 2500 Hz or 20000 Hz.

As mentioned above, the central nervous magnetic stimulation device can generate a magnetic field with an approximately uniform magnetic field intensity within the entire area of head, which can act on the deep brain, and at the same time, the time-varying current is output at a frequency above 2000 Hz and constitutes a string of rhythmic cluster-like bursts at an appropriate duty ratio, or forms an envelope in a difference frequency way to output rhythm characteristics. With such a design, a relatively smaller peak current and a weaker peak magnetic field intensity can be used to achieve a same or even better biological treatment effect. Moreover, the relatively weak current and magnetic field can reduce an operation noise of a product, and can also help to design a miniaturized, even portable, product with a low cost, bringing a better user experience.

Wherein, the control circuit 101 can output to the coil component 103 a time-varying current with a fixed period and an accurate waveform, to generate a period of time-varying magnetic field with an accurate waveform, and to constitute a rhythmic magnetic stimulation string with cluster-like bursts by designing the number of periods for the outputs and pauses of a waveform, wherein the magnetic stimulation string can be presented intermittently, for example, 8-second pause per 2-second operation. Wherein, the rhythm of the string with the rhythmic cluster-like bursts can be achieved by different settings of the duty ratio, which can be set according to the needs of the healthcare or medical treatment, to obtain better biological effects.

Wherein, the rhythm of the string with the rhythmic cluster-like bursts can be a delta rhythm (generally less than 3 Hz), a theta rhythm (generally referring to 4~8 Hz), an alpha rhythm (generally referring to 8~12 Hz), a beta rhythm (generally referring to 20 Hz), or a gamma rhythm generally comprising a low-frequency stage of gamma rhythm (generally referring to 30~60 Hz) and a high-frequency stage of gamma rhythm (generally referring to 60~120 Hz).

In some embodiments, the control circuit 101 comprises a main control chip and a main circuit; wherein, the main circuit mainly comprises a fully-controlled semiconductor device and peripheral circuits thereof, and outputs a pulse width modulation voltage to the coil component 103 so that the coil component 103 can output a current with a designed waveform to induce a magnetic field.

The control circuit 101 may also comprise a data interface to receive operating instructions. The data interface generally comprises a wireless communication chip or module. The actual operation of the central nervous magnetic stimulation device can be operated based on the operation parameters preset in the main control chip or according to the instructions received by the data interface.

The control circuit 101 is connected to the coil component 103, and can output a time-varying current to excite the coil component 103, so as to generate a time-varying magnetic field.

The power source 102 is used to supply power to the control circuit 101. The power source 102 may specifically be a power adapter or a rechargeable battery pack. Specifically, the power source 102 supplies the control circuit 101 with a DC voltage below 60V to improve electrical safety of the product. For example, the supplied voltage is specifically 12~24V.

In some embodiments, the coil component 103 comprises a plurality of coils, each having independent output parameters. The output parameters comprise a size of a peak value, a frequency rhythm, a waveform, and a phase of the time-varying current.

The arrangement design of the coil component 103 should be made such that the coil component 103 can generate a time-varying magnetic field with an approximately uniform intensity distribution within the target area corresponding to the size of the brain.

Wherein, the arrangement design of the coil component 103 comprises the number, a shape, a turns, and a size of the coils, the position settings of the coils, and the distance between the coils each other. For example, the coil can be designed as a circle, an ellipse, a square, or a rectangle, with a relatively large magnetic flux area, such as more than 50 square centimeters, so that an intensity gradient of the magnetic field received by the entire brain can be as small as possible.

When the coil component 103 comprises a plurality of coils, each coil can be controlled to generate an output synchronously, that is, the time-varying magnetic field generated by the time-varying current output by each coil has the same frequency and phase.

In practice, the plurality of coils of the coil component 103 can also be divided into several groups as needed, and the coils in each group generate outputs synchronously or in a difference frequency way. In addition, different groups can output rhythm characteristics synchronously at an appropriate duty ratio, or output rhythm characteristics by forming an envelope in a difference frequency way.

For example, the difference frequency way defines the frequency difference of 40 Hz between two pairs of coils, which output (2500+20) Hz and (2500−20) Hz respectively.

Specifically, different modes and operation sequences of coil groups can be determined according to the user's state, or different modes of coil groups can be determined according to different time periods, to achieve different magnetic stimulation modes.

It should be pointed out that, in a state where the coil groups operate asynchronously, the coils in the coil groups may have overlapping parts according to the use requirements. Taking three coils as an example, the first coil and the second coil can be combined as one coil group, while the second coil and the third coil can be combined as another coil group. During operation, the first coil and the second coil can be first combined for output, then the second coil and the third coil can be combined for output, and certainly vice versa, which is determined according to the usage requirements. It should also be noted that the first coil and the third coil can also be combined as one coil group.

It should also be noted that when actually designing the product, the coil component 103 can be designed as only one large-size coil, the size of which matches with the overall size of the brain. For example, the coil can be designed as a circular coil with a diameter of 20 cm or more, to make the intensity of the magnetic field received by the whole brain approximately uniform.

Figure 2:
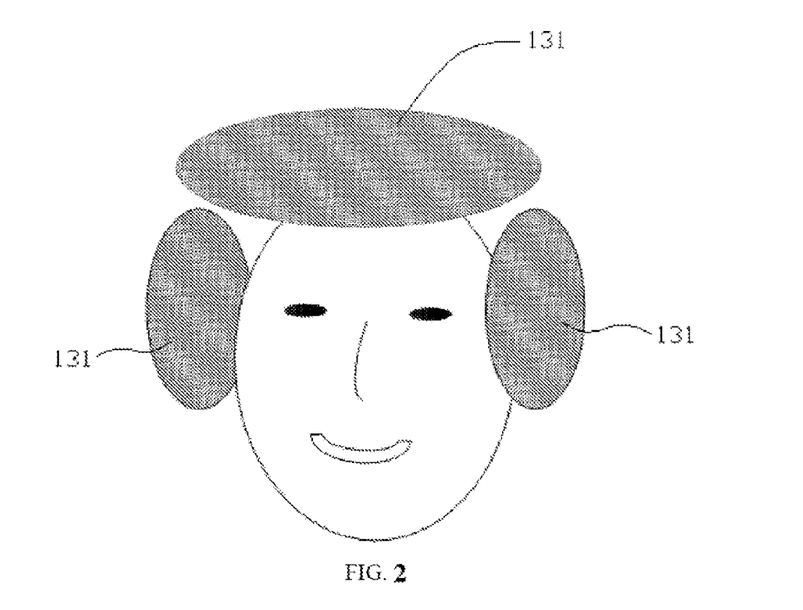
FIG. 2 illustrates a brief schematic diagram of a coil distribution with a three-coil structure of a coil component, according to an embodiment.

In some embodiments, the coil component 103 may only comprise three coils 131. When specifically arranged, the three coils correspond to positions of temporal lobes on both sides of the brain and occipital lobe respectively, correspond to positions of temporal lobes on both sides of the brain and parietal lobe respectively, or correspond to positions of temporal lobes on both sides of the brain and frontal lobe respectively. With reference to FIG. 2, FIG. 2 illustrates a brief schematic diagram showing that the three coils 131 are arranged on positions of the temporal lobes on both sides of the brain and the frontal lobe respectively.

Similarly, during the treatment, the three coils can be combined into different forms of coil groups, and different groups can be operated in sequence according to the treatment needs.

Figure 3:
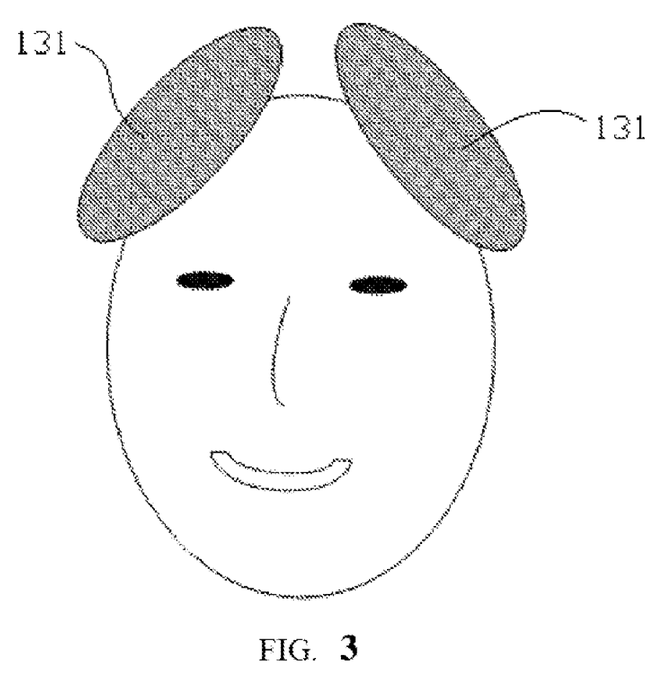
FIG. 3 illustrates a brief schematic diagram of a coil distribution with a two-coil structure of a coil component, according to an embodiment.

In some embodiments, the coil component 103 may only comprise two coils 131. When specifically arranged, the two coils correspond to left and right sides of the brain respectively, as shown in FIG. 3, or correspond to positions of occipital lobe and parietal lobe respectively.

When to be actually set, the two coils 131 of the coil component 103 may be located at the top of the head in parallel, for example, one coil may be located near the top of the head, while the other coil may be located slightly away from the top of the head.

In some embodiments, the diameter of the coil 131 is greater than the outer diameter of the human brain, and the distance between the two coils 131 is greater than the radius of the coil 131 and less than 3 times of the radius of the coil 131.

In addition, the coil component 103 may also be provided with a form of two above-mentioned coil groups, that is, the coil component 103 comprises two coil groups, wherein each coil group comprises only two coils 131, and the two coils 131 of each coil group are arranged at the above-mentioned positions, i.e. corresponding to left and right sides of the brain respectively, or corresponding to positions of occipital lobe and parietal lobe respectively, or are located at the top of the head in parallel. Specifically, the two coil groups may be partially overlapped or not overlapped at all, and the two coil groups output in a difference frequency way.

In some embodiments, the waveform of the time-varying current output by the control circuit 101 may be a trapezoidal wave, a sine wave, or a triangle wave. And the waveform of the time-varying magnetic field ultimately generated by the control coil component 103 may be one waveform or a combination of two waveforms, which are determined according to specific needs.

In some embodiments, the waveform of the time-varying magnetic field generated by the coil component 103 has a rising edge and/or a falling edge, where the rising edge of the waveform may be a straight line, a slope of which may be determined by matching a power source voltage of the product and parameters of coil. Of course, when the voltage is relatively lower and the coil inductance is larger, the rising edge of the waveform can also be a curve. Accordingly, the falling edge of the waveform can also be a straight line or a curve.

When the waveform of the time-varying magnetic field generated by the coil component 103 has both a rising edge and a falling edge, there is a platform between the rising edge and the falling edge, the duration of which can be set according to requirements, for example, the duration corresponding to the platform may tend to zero.

In addition, the waveform of the time-varying current output by the control circuit 101 may be unipolar or bipolar as needed.

In some embodiments, the peak intensity of the time-varying magnetic field is greater than 0.5 Gs and less than 100 Gs within the target area, i.e. the action area, and the change rate of the peak intensity of the time-varying magnetic field over time dB/dt within the action area is less than 35 T/s.

More specifically, the maximum value of the peak intensity of the time-varying magnetic field within the action area matching the brain is greater than 0.5 Gs and less than 20 Gs.

Figure 4:
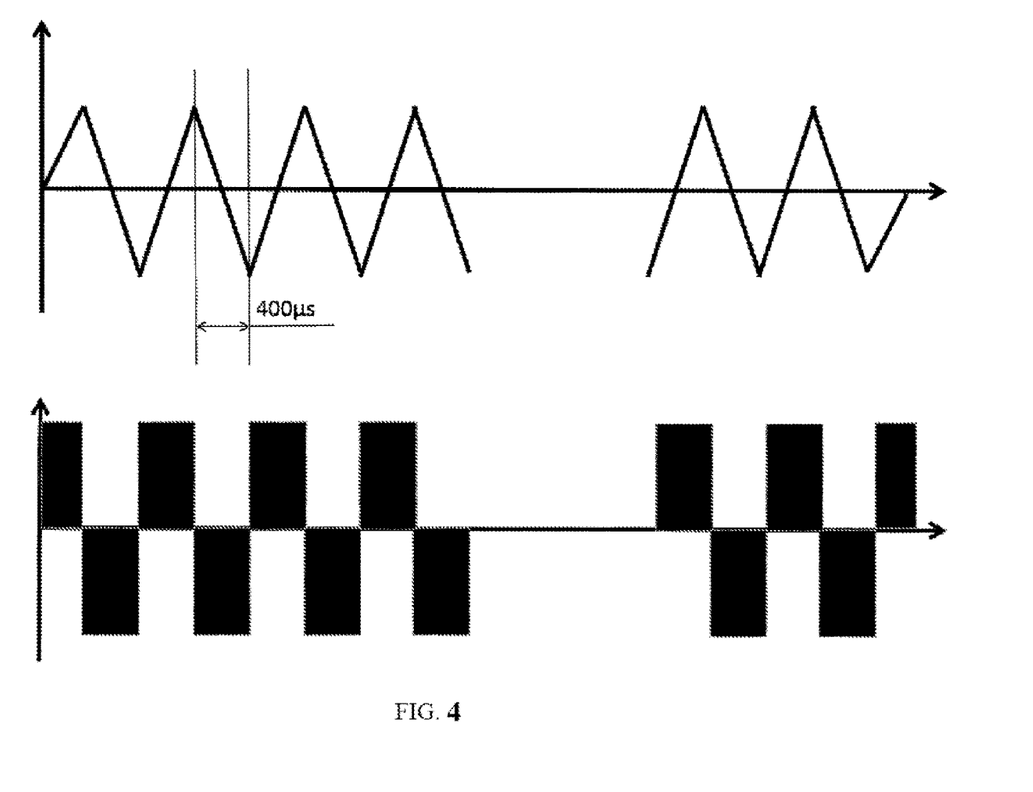
FIG. 4 illustrates a schematic waveform diagram of current or induced magnetic field and corresponding induced electric field thereof, according to an embodiment.

Please refer to FIG. 4, which illustrates a schematic diagram of waveforms of current or induced magnetic field and corresponding induced electric field thereof, according to an embodiment.

In FIG. 4, the upper waveform illustrates the waveform of current or induced magnetic field, illustratively as a waveform of a triangle wave, in which the induced electric field has a period of 400 us and the frequency of 2500 Hz.

Figure 5:
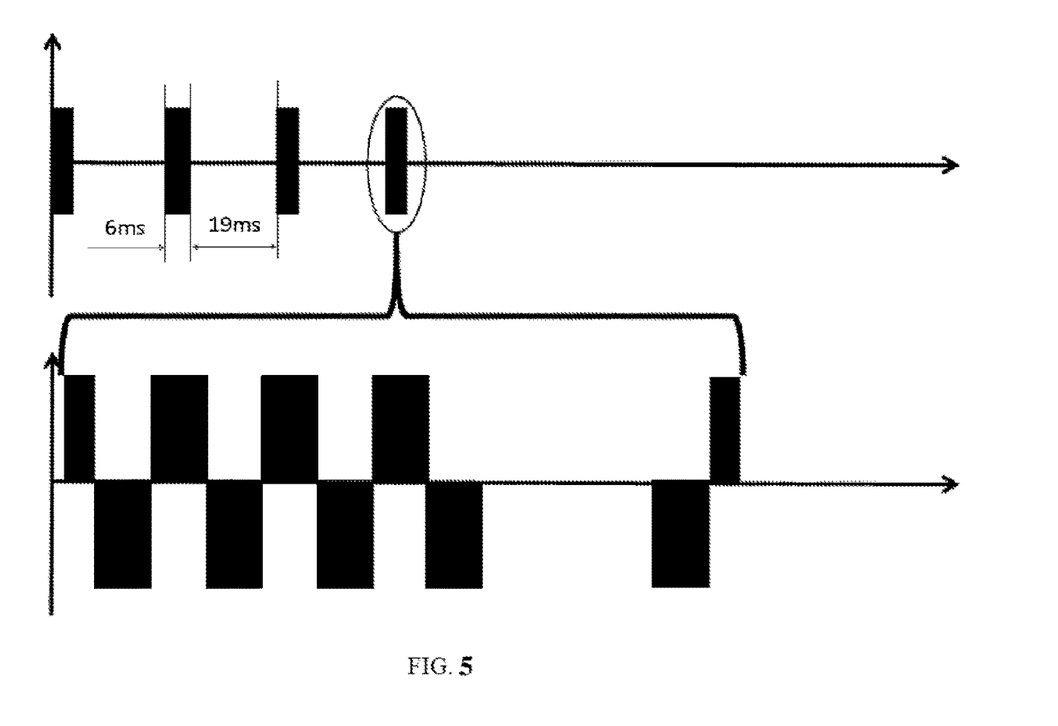
FIG. 5 illustrates a schematic waveform diagram of a magnetically induced electric field with gamma-rhythmic cluster-like bursts, according to an embodiment.

Please refer to FIG. 5, which illustrates a schematic diagram of a waveform of magnetically induced electric field with a gamma-rhythmic cluster-like bursts, according to an embodiment.

In FIG. 5, the time-varying current with a period of 100 us has an output of 6 ms, and a pause of 19 ms, and then outputs a magnetic stimulation of 40 Hz with rhythmic cluster-like bursts.

During specific operation, the magnetic stimulation can also be designed as an intermittent, rhythmic stimulation with cluster-like bursts. For example, 10-second output of such rhythmic cluster-like bursts include 2-second operation and 8-second pause (where the intermittent part is not shown in the FIG. 5).

In addition to the aforementioned central nervous magnetic stimulation device, the disclosure also provides a healthcare or medical instrument comprising the central nervous magnetic stimulation device. The healthcare or medical instrument is used to improve brain function, prevent or treat brain disease; or, the healthcare or Medical instrument is used in combination with certain medicines to improve brain function, prevent or treat brain diseases, or to enhance the effects of medicines or reduce side effects caused by medicines.

In specific applications, the medicines used in combined with the instrument may comprise cholinesterase inhibitors, selective glutamatergic receptor antagonists, various antipsychotic medicines, various antidepressants, various mood stabilizers, various 13 secretase inhibitors or modulators, various gamma secretase inhibitors or regulators, or various anti-inflammatory medicines, etc. The specific scheme for joint application is determined after determining the effect of the joint application through basic research and clinical research.

The central nervous magnetic stimulation device and the healthcare or medical instrument having same provided by the disclosure have been described in details above. Specific examples are used to explain the principles and implementations of the disclosure herein. The descriptions of the above embodiments are only used to help to understand the method and the core concept of the disclosure. It should be noted that for those of ordinary skill person in the art, several improvements and modifications may be made without departing from the principle of the disclosure, which fall within the scope of the claims of the disclosure.

The invention claimed is:

1. A central nervous magnetic stimulation device, configured for use as a health care or medical device, comprising: a power source, a control circuit and a coil component; wherein, the control circuit comprises a main control chip and a main circuit, the power source supplies power to the control circuit, and the control circuit outputs a time-varying current to the coil component to generate a corresponding time-varying magnetic field;
wherein an action area of the time-varying magnetic field is configured to cover an area that equals the size of a user's head, and the time-varying current is output at a frequency of 2000 Hz-20,000 Hz, and constitutes a string of rhythmic cluster bursts at an appropriate duty ratio;
wherein the coil component comprises at least two coils configured to function simultaneously; and
wherein a maximum value of a peak intensity of the time-varying magnetic field within the action area that is configured to cover an area that equals the size of the user's head is greater than 0.5 Gs and less than 20 Gs, and a change rate of the peak intensity of the time-varying magnetic field over time (dB/dt) within the action area is less than 35 T/s.

2. The central nervous magnetic stimulation device according to claim 1, wherein a rhythmic output of the time-varying current has an intermittent characteristic.

3. The central nervous magnetic stimulation device according to claim 1, wherein the coil component comprises the at least two coils, and outputs of the coils are independent of each other;
wherein the at least two coils are divided into different groups and
each group generates outputs synchronously at the duty ratio or by forming an envelope which represents superimposed magnetic fields in different frequencies;
wherein the coil component is configured to correspond to positions on a brain selected from the group consisting of temporal lobes on both sides of the brain, a occipital lobe a parietal lobe, a frontal lobe, and at a top of the brain respectively;
and
wherein the different groups are partially overlapped or not overlapped.

4. The central nervous magnetic stimulation device according to claim 3, wherein a waveform of the time-varying current is a trapezoidal wave, a sine wave, or a triangle wave, and the time-varying magnetic field is one waveform or a combination of two or more waveforms.

5. The central nervous magnetic stimulation device according to claim 1, wherein a waveform of the time-varying magnetic field generated by the coil component has a rising edge and/or a falling edge and a platform between the rising edge and/or the falling edge.

6. The central nervous magnetic stimulation device according to claim 5, wherein a duration corresponding to the platform between the rising edge and the falling edge in the waveform of the time-varying magnetic field generated by the coil component is zero.

7. The central nervous magnetic stimulation device according to claim 1, wherein a rhythm of the string of the rhythmic cluster bursts is specifically a delta rhythm, a theta rhythm, an alpha rhythm, a beta rhythm, or a gamma rhythm of brain waves.

8. The central nervous magnetic stimulation device according to claim 1, wherein the frequency of the time-varying current is about 2500 Hz.

9. The central nervous magnetic stimulation device according to claim 1, wherein the power source supplies the control circuit with a direct current voltage of 60V or less.

10. The central nervous magnetic stimulation device according to claim 9, wherein the power source supplies the control circuit with a direct current voltage of 12 to 36V.

11. The central nervous magnetic stimulation device according to claim 9, wherein the power source supplies the control circuit with a direct current voltage of 24V.

* * * * *